(12) United States Patent
Konomura

(10) Patent No.: US 10,016,118 B2
(45) Date of Patent: Jul. 10, 2018

(54) ENDOSCOPE GUIDE TUBE AND ENDOSCOPE

(71) Applicant: OLYMPUS CORPORATION, Tokyo (JP)

(72) Inventor: Yutaka Konomura, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 125 days.

(21) Appl. No.: 15/008,899

(22) Filed: Jan. 28, 2016

(65) Prior Publication Data

US 2016/0143513 A1    May 26, 2016

Related U.S. Application Data

(63) Continuation of application No. PCT/JP2014/060719, filed on Apr. 15, 2014.

(30) Foreign Application Priority Data

Jul. 31, 2013   (JP) ................................ 2013-159347

(51) Int. Cl.
*A61B 1/00* (2006.01)
*G02B 23/24* (2006.01)
(Continued)

(52) U.S. Cl.
CPC ........ *A61B 1/00154* (2013.01); *A61B 1/0014* (2013.01); *A61B 1/0055* (2013.01); *A61B 1/00057* (2013.01); *G02B 23/2476* (2013.01)

(58) Field of Classification Search
CPC . A61B 1/00154; A61B 1/0014; A61B 1/0055; A61B 1/00057; A61B 1/00142;
(Continued)

(56) References Cited

U.S. PATENT DOCUMENTS 5,301,061 A    4/1994  Nakada et al.

FOREIGN PATENT DOCUMENTS

EP    0 098 100 A2    1/1984
JP    3-59509 A    3/1991
(Continued)

OTHER PUBLICATIONS

International Search Report dated Jul. 29, 2014 issued in PCT/JP2014/060719.
(Continued)

*Primary Examiner* — Timothy J Neal
(74) *Attorney, Agent, or Firm* — Scully, Scott, Murphy & Presser, P.C.

(57) ABSTRACT

An endoscope guide tube includes a tube member including a live part, the tube member being constructed by including a tube body that makes up an outer layer and a braid that braids, into a tubular form, wound metal members and insulating members wound in a direction opposite to a winding direction of the metal members, a connection member provided with a first contact connecting ends of the metal members and a second contact connecting ends of the metal members, at least one of a first contact side conduction detection section that detects that the live part contacts the metal members and a second contact side conduction detection section, and a signal output section that outputs a notification signal to a notification section.

16 Claims, 8 Drawing Sheets

(51) Int. Cl.
*A61B 1/005* (2006.01)
*A61B 1/04* (2006.01)

(58) Field of Classification Search
CPC ............ A61B 1/00055; A61B 1/00135; A61B 1/00059; A61B 1/00062; A61B 1/00105; A61B 1/00124; G02B 23/2476
See application file for complete search history.

(56) References Cited

FOREIGN PATENT DOCUMENTS

| | | |
|---|---|---|
| JP | 3-236825 A | 10/1991 |
| JP | 7-344 A | 1/1995 |
| JP | 7-51227 A | 2/1995 |
| JP | 2004-205764 A | 7/2004 |
| JP | 2007-020938 A | 2/2007 |

OTHER PUBLICATIONS

Extended Supplementary European Search Report dated Feb. 28, 2017 in related European Patent Application No. 14 83 2126.8.

ENDOSCOPE GUIDE TUBE AND ENDOSCOPE

CROSS REFERENCE TO RELATED APPLICATION

This application is a continuation application of PCT/JP2014/060719 filed on Apr. 15, 2014 and claims benefit of Japanese Application No. 2013-159347 filed in Japan on Jul. 31, 2013, the entire contents of which are incorporated herein by this reference.

BACKGROUND OF THE INVENTION

1. Field of the Invention

The present invention relates to an endoscope guide tube and an endoscope including a tube member provided with a braided tube constructed by including an insulating member making up an outer layer and a metal wire making up an inner layer thereof.

2. Description of the Related Art

Endoscopes are used in the medical field and the industrial field or the like. Endoscopes used in the industrial field can check for damage, corrosion and the like with a flexible elongated insertion portion thereof inserted into a jet engine, plant piping or the like.

In recent years, along with the popularization of electric cars, there is a demand for endoscopic observation of the interior of a device including many live parts or the interior of a device including a switchboard.

The insertion portion may be made of an insulating member to be able to safely observe the interior of the device including live parts using the endoscope.

The insertion portion of an endoscope is generally constructed by connecting a distal end portion, a bending portion and a flexible tube portion. Construction of the insertion portion using only an insulating member allows endoscopic observation of the interior of a device including many live parts to be carried out in a worry-free and safe manner.

Japanese Patent Application Laid-Open Publication No. 3-236825 discloses an endoscope provided with water leakage detection means. In this endoscope, a cylindrical water sensor is externally provided on the outside of a substrate so as to be able to detect water. In the water sensor, a positive electrode and a negative electrode are spirally wound in parallel around the perimeter of an insulating cylindrical member, the ends of the respective electrodes are connected to signal lines for water leakage detection, and the signal lines are connected to a water leakage detection circuit. According to this technique, when a water droplet adheres to and spans the positive electrode and the negative electrode, the water leakage detection circuit can detect that the electrodes are electrically connected.

SUMMARY OF THE INVENTION

An endoscope guide tube according to an aspect of the present invention includes a tube member to be inserted into a device including a live part, the tube member being constructed by including a tube body made of an insulating member that makes up an outer layer and a braid that makes up an inner layer of the tube body, and braids, into a tubular form, metal members wound clockwise or counterclockwise with a plural number of carriers including a predetermined number of ends in parallel and insulating members wound with a plural number of carriers including a predetermined number of ends in a direction opposite to a winding direction of the metal members in parallel, a connection member provided with a first contact electrically connecting in a bundled manner ends of the metal members in substantially half the carriers in number of the plural metal members making up the tube member and a second contact electrically connecting in a bundled manner ends of the metal members with the remaining carriers in number of the plural metal members, and at least one of a first contact side conduction detection section that detects that the live part contacts the metal members connected to the first contact and a second contact side conduction detection section that detects that the live part contacts the metal members connected to the second contact.

The endoscope according to the aspect of the present invention is provided with the configuration of the endoscope guide tube.

DETAILED DESCRIPTION OF THE PREFERRED EMBODIMENTS

Hereinafter, an embodiment of the present invention will be described with reference to the accompanying drawings.

An embodiment of the present invention will be described with reference to FIG. 1 to FIG. 6.

Figure 1:
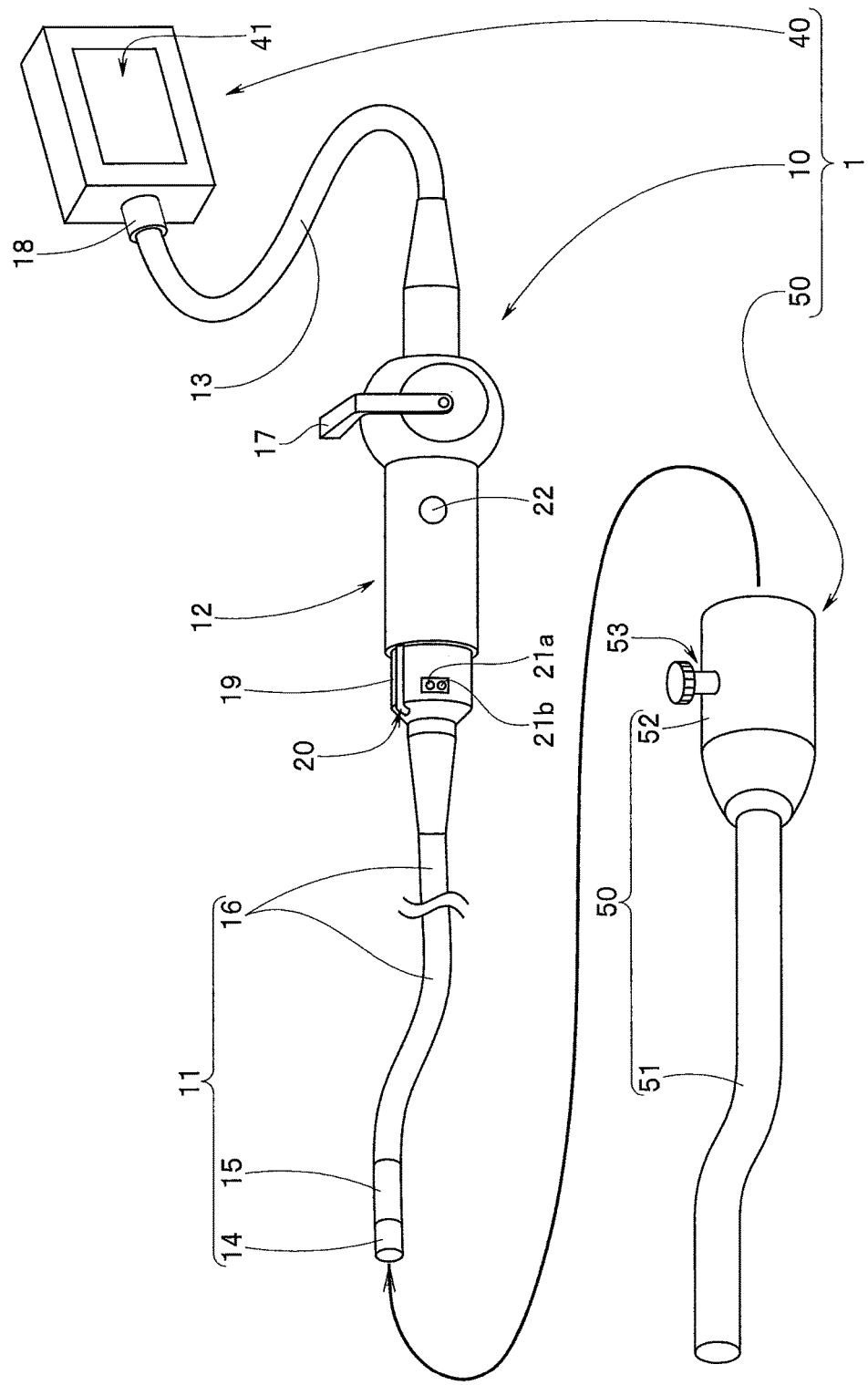
FIG. 1 is a diagram describing an endoscope system provided with an endoscope and an endoscope guide tube.

An endoscope system 1 shown in FIG. 1 is constructed by including an electronic endoscope (hereinafter abbreviated as "endoscope") 10, an apparatus body 40, and an endoscope guide tube 50.

The endoscope 10 is constructed by mainly including an endoscope insertion portion 11, an operation portion 12 provided on a proximal end side of the endoscope insertion portion 11, a universal cord 13 that extends from this operation portion 12.

The endoscope insertion portion 11 is constructed by connecting a rigid distal end portion 14, a bendable bending portion 15, and a flexible tube portion 16 provided with flexibility in order from the distal end side.

The distal end portion 14 is made of, for example, ceramic having insulating properties and provided with an image pickup optical system (not shown), an illumination optical system (not shown) or the like.

Figure 2A:
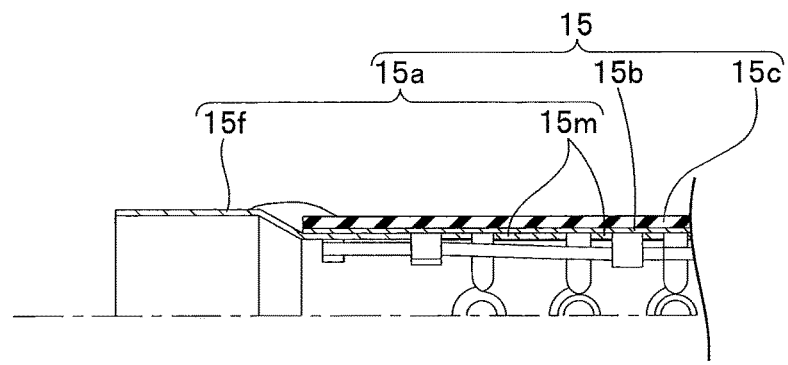
FIG. 2A is a diagram describing a bending portion of the endoscope provided with a braid in an inner layer of an insulating member making up an outer layer.

As shown in FIG. 2A, the bending portion 15 is configured to bend in two directions: up and down, for example. The bending portion 15 is constructed by laminating one metallic distal end bending piece 15f, a plurality of intermediate bending piece sets 15m, a bending piece set 15a configured to bend up and down by rotatably connecting a proximal end bending piece (not shown), a braid 15b which is a metallic braided tube that covers the outer layer of the plurality of intermediate bending piece sets 15m, and a bending tube 15c which is a tube body made of an insulating member that covers the outer layer of the braid 15b.

Note that the bending portion 15 is not limited to the configuration in which it is bent in two directions: up and down, but may have a configuration in which it is bent in four directions: up, down, left and right.

Figure 2B:
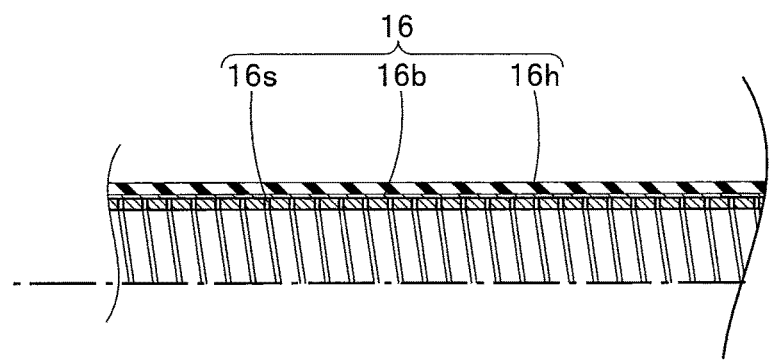
FIG. 2B is a diagram describing a flexible tube portion of the endoscope provided with a braid in an inner layer of an insulating member making up an outer layer.

As shown in FIG. 2B, the flexible tube portion 16 is configured by laminating a spiral tube 16s made of a metallic steel sheet which constitutes a core member, a braid 16b that covers the outer layer of the spiral tube 16s and a heat shrinkable tube 16h which is the tube body that covers the outer layer of the braid 16b.

As shown in FIG. 1, the operation portion 12 of the endoscope 10 is provided with a bending operation knob 17 for bending the bending portion 15, and various switches which are not shown such as a freeze switch and a release switch.

A mounting section 19 is provided on the distal end side of the operation portion 12, in which an integral fixing section 52 which will be described later of the endoscope guide tube 50 is disposed. A positioning mounting groove 20 is formed at a predetermined position of the outer circumferential face of the mounting section 19.

Note that a second detection section 70 and a third detection section 80 which will be described later are provided in the operation portion 12. Reference numeral 21a denotes a mounting section first electric contact which will be described later, reference numeral 21b denotes a mounting section second electric contact which will be described later, and reference numeral 22 denotes a notification section, which is a notification lamp and will be described later.

The universal cord 13 is configured so that its proximal end portion is detachably attached to the apparatus body 40 via a connector 18. The apparatus body 40 is an endoscope control apparatus that serves as both a light source apparatus and a video processor, and is provided with a display section 41, a control section (not shown) including an image processing circuit, a power source section (not shown), and the like.

The endoscope guide tube 50 is constructed by including a tube insertion portion 51 and an integral fixing section 52 provided on the proximal end side of the tube insertion portion 51. The tube insertion portion 51 of the endoscope guide tube 50 is a tube member inserted into a device including a live part. For this reason, the endoscope guide tube 50 is configured, when an insulating member making up an outermost layer of the tube insertion portion 51 is broken, so as to be able to detect the occurrence of the breakage. Reference numeral 53 denotes an attachment/detachment section which is disposed at a predetermined position of the integral fixing section 52.

The tube insertion portion 51 is a flexible and tubular tube member and the endoscope insertion portion 11 is inserted therein.

Figure 2C:
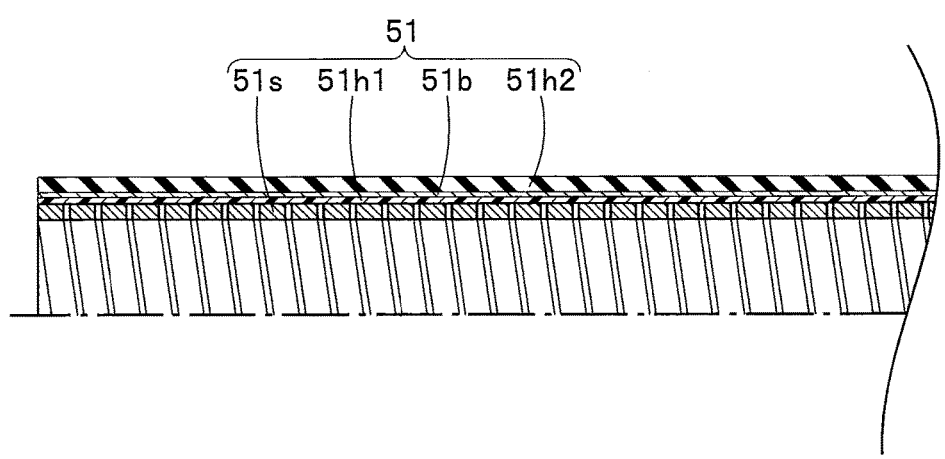
FIG. 2C is a diagram describing a tube insertion portion of an endoscope guide tube provided with a braid in an inner layer of the insulating member making up the outer layer.

As shown in FIG. 2C, the tube insertion portion 51 is constructed by laminating a spiral tube 51s made of a metallic steel sheet which serves as a core member, a first heat shrinkable tube 51h1 that covers an outer layer of the spiral tube 51s, a braid 51b for making up a contact side conduction detection section which will be described later that covers an outer layer of the first heat shrinkable tube 51h1, and a second heat shrinkable tube 51h2 that covers an outer layer of the braid 51b. The second heat shrinkable tube 51h2 which is the tube body makes up the outermost layer of the tube insertion portion 51.

A configuration of the braid 51b will be described with reference to FIG. 3A to FIG. 3C.

Figure 3A:
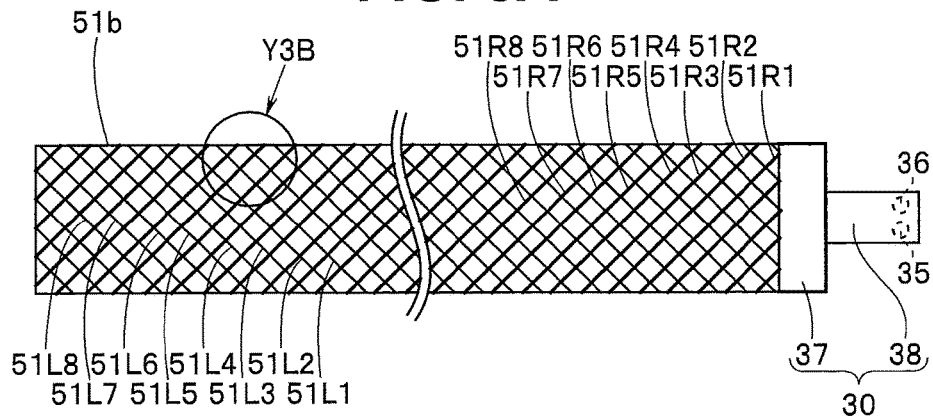
FIG. 3A is a diagram describing the braid making up the tube insertion portion of the endoscope guide tube.
Figure 3B:
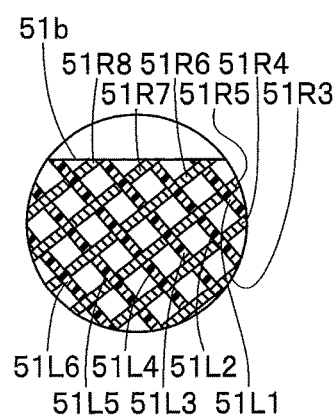
FIG. 3B is an explanatory diagram showing an enlarged view of the portion shown by an arrow Y3B in FIG. 3A.

As shown in FIG. 3A and FIG. 3B, the braid 51b is a braided tube obtained by braiding a metal wire 51R which is a clockwise wound metal member and an insulating wire 51L which is a counterclockwise wound insulating member into a tubular form. The metal wire 51R is, for example, a stainless steel elemental wire and the insulating wire 51L is a polyimide elemental wire.

Note that the metal wire 51R is not limited to the stainless steel elemental wire, but may also be a tungsten wire or the like. The insulating wire 51L is not limited to the polyimide elemental wire, but may also be another resin elemental wire. Furthermore, the braided tube may be configured by winding the metal wire counterclockwise and winding the insulating wire clockwise.

In the present embodiment, a wire diameter of the elemental wire of one metal wire 51R has a predetermined diameter and the number of ends is, for example, three. On the other hand, a wire diameter of the elemental wire of one insulating wire 51L has a predetermined diameter and the number of ends is, for example, five.

As a result, when tensile strength (also described as "tension") of the metal wire 51R and tensile strength of the insulating wire 51L are adjusted so as to substantially match and the braid 51b is set to be in a desired balance state.

Note that the metal member is not limited to the metal wire but may be a metallic band-shaped member or the like. The insulating member is not limited to the insulating wire either, but may be a resin band-shaped member or may be a resin tube having a through hole or a groove in which the metal member is disposed.

The number of carriers of the braid 51b is, for example, 16 and the braid 51b is configured by arranging in parallel and winding clockwise eight carriers of metal wires 51R1, 51R2, ..., 51R7 and 51R8, and arranging in parallel and winding counterclockwise eight carriers of insulating wires 51L1, 51L2, ..., 51L7 and 51L8.

According to the aforementioned configuration, a predetermined distance is kept between the neighboring metal wires 51R without contacting each other.

Note that the number of carriers is not limited to 16, but may be more or less than 16. The number of carriers is not limited to an even number, but may be an odd number.

Moreover, the wire diameter of the metal elemental wire and the wire diameter of the insulating wire elemental wire are set as appropriate and tension of each wire is adjusted or the number of ends of the metal wire 51R and the number of ends of the insulating wire 51L may be set as appropriate to adjust tension of each wire.

Figure 3C:
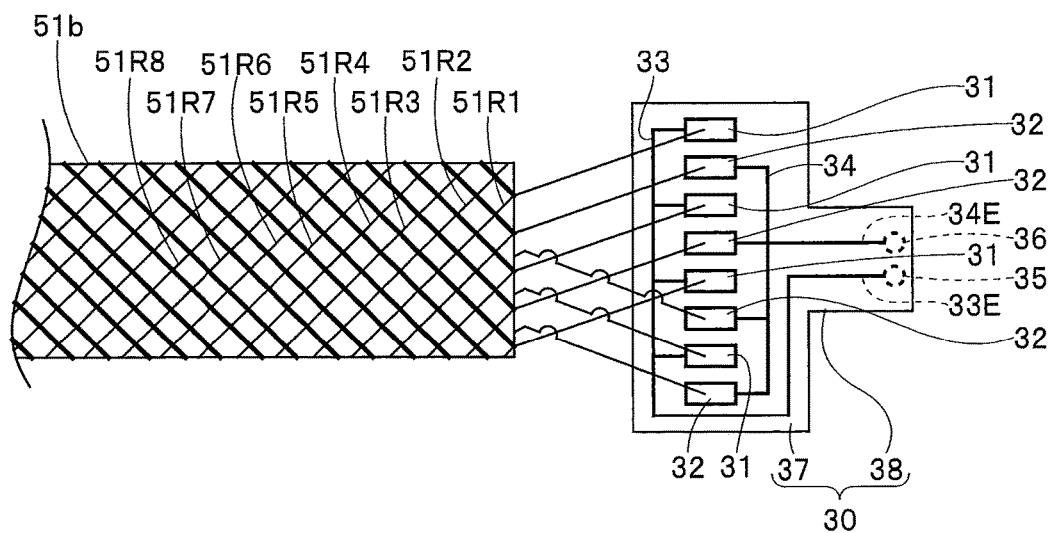
FIG. 3C is a diagram describing a connection relationship between the metal wires of the braid and a flexible substrate.

As shown in FIG. 3A and FIG. 3C, a tube-shaped flexible substrate 30 is provided at a proximal end portion of the tube insertion portion 51.

The flexible substrate 30 is a connection member and constructed by including a tube-shaped substrate body 37 and an extending substrate section 38 which constitutes an extending section.

The substrate body 37 is provided with a plurality of first connection sections 31, a plurality of second connection sections 32, a plurality of first wirings 33, and a plurality of second wirings 34. The first connection section 31 and the second connection section 32 of the flexible substrate 30 are provided at positions at which they contact the corresponding metal wires 51RR. Necessary connections can be made by only pressing the flexible substrate 30 against the braid 51*b*. The first connection sections 31 and the second connection sections 32 may also be forming by tilting them in accordance with the braid 51*b*. The extending substrate section 38 is provided with a first wiring end portion 33E, a first contact 35, a second wiring end portion 34E, and a second contact 36.

Proximal end portions of half the plurality of metal wires 51R1, . . . , 51R8, for example, metal wires 51R1, 51R3, 51R5 and 51R7 arrayed in odd numbers are connected to the plurality of first connection sections 31 respectively. Proximal end portions of the remaining metal wires, that is, metal wires 51R2, 51R4, 51R6 and 51R8 arrayed in even numbers are connected to the plurality of second connection sections 32 respectively.

The first wiring 33 is a wiring that extends from each first connection section 31. The second wiring 34 is a wiring that extends from each second connection section 32.

The first wiring end portion 33E is one wiring that extends to the first contact 35 by bundling the proximal end sides of the plurality of first wirings 33. The second wiring end portion 34E is one wiring that extends to the second contact 36 by bundling the proximal end sides of the plurality of second wirings 34.

The first contact 35 is provided at a predetermined position on the proximal end side of the first wiring end portion 33E and the second contact 36 is provided at a predetermined position on the proximal end side of the second wiring end portion 34E. The extending substrate section 38 provided with the first contact 35 and the second contact 36 is disposed at a predetermined position of an inner surface of the integral fixing section 52.

When the integral fixing section 52 is disposed in the mounting section 19, the first contact 35 and the mounting section first electric contact 21*a* are directly or indirectly electrically connected, and the second contact 36 and the mounting section second electric contact 21*b* are directly or indirectly electrically connected.

The integral fixing section 52 is made of, for example, a rigid resin member and a proximal end portion of the tube insertion portion 51 is fixed to an end of the distal end side of the integral fixing section 52. The integral fixing section 52 is a cylindrical member detachably disposed on the mounting section 19 provided on the distal end side of the operation portion 12 of the endoscope 10.

Figure 4:
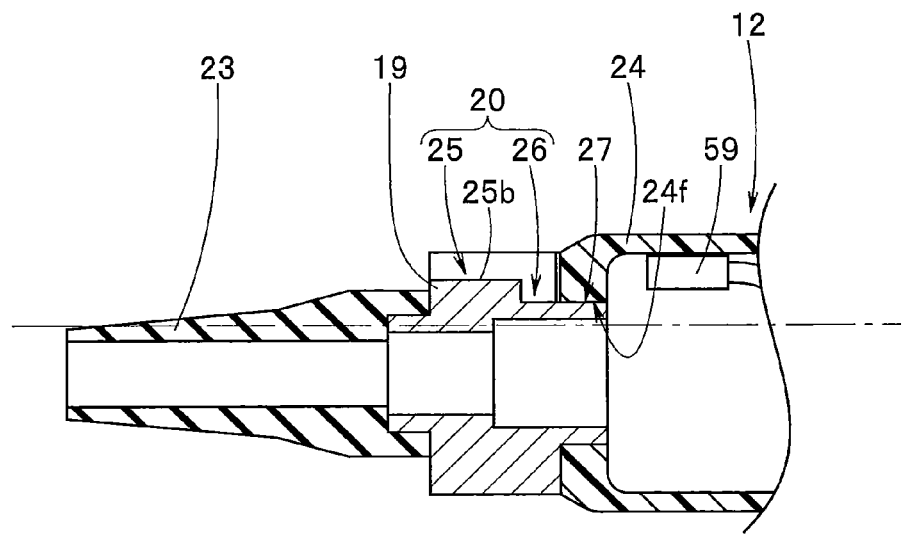
FIG. 4 is a diagram describing a mounting section provided on a distal end side of an operation portion.

As shown in FIG. 4, a bend-preventing member 23 is fixed on a distal end side portion of the mounting section 19 making up the distal end side of the operation portion 12. A distal end side portion of the distal end side operation portion body 24 making up the distal end side of the operation portion 12 is fixed to the proximal end side portion of mounting section 19.

The positioning mounting groove 20 is constructed by including a guide groove 25 and a locking hole 26. The guide groove 25 is elongately formed along a longitudinal axis direction of the operation portion. The locking hole 26 is a dent formed in a bottom surface 25*b* of the guide groove 25, in which a distal end portion of a stopper (reference numeral 54 in FIG. 5) making up the attachment/detachment section 53 is accommodated. Reference numeral 27 denotes a proximal end side small diameter portion and a distal end side portion inner surface 24*f* of the distal end side operation portion body 24 is disposed at the proximal end side small diameter portion 27.

Reference numeral 59 denotes a transmission coil which will be described later and constitutes a non-contact power supply section (see reference numeral 61 in FIG. 6 or the like) provided opposite to a reception coil which will be described later (see reference numeral 28 in FIG. 5).

Figure 5:
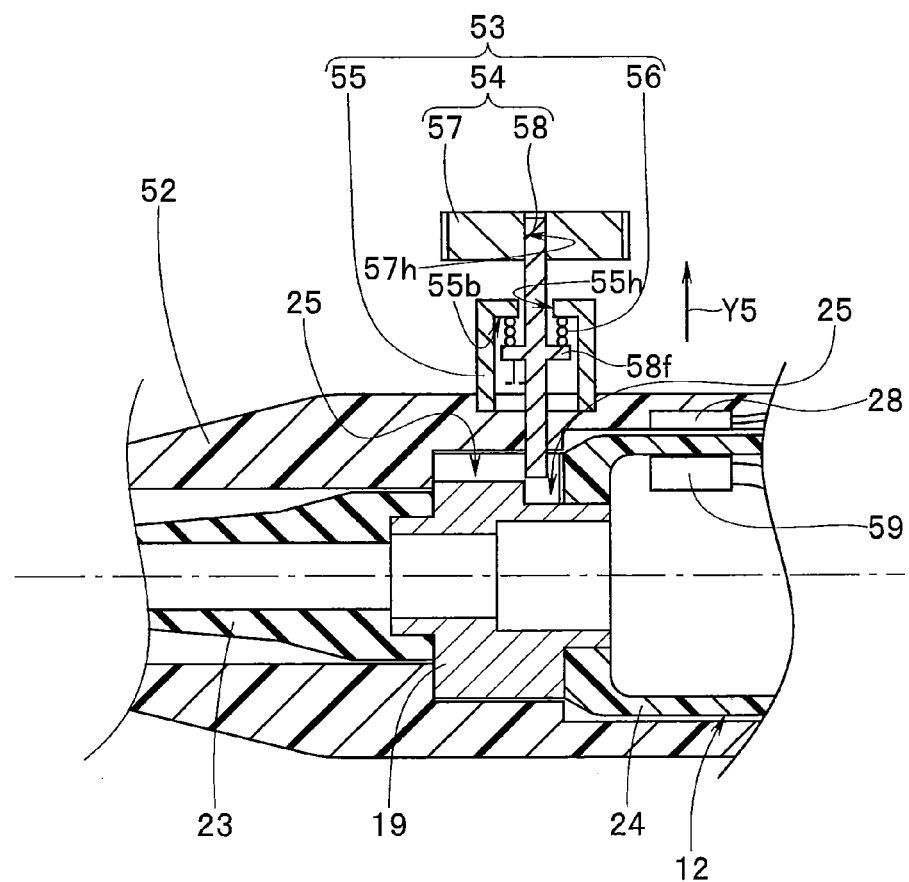
FIG. 5 is a diagram describing a relationship between an integral fixing section of the endoscope guide tube and the mounting section of the operation portion and a configuration of an attachment/detachment section provided in the integral fixing section.

As shown in FIG. 5, the attachment/detachment section 53 is constructed by including a stopper 54, a stopper arrangement member 55 and a spring 56. The stopper 54 is constructed by including a holding member 57 and a shaft member 58. The holding member 57 includes a center through hole 57*h*. One end portion of the shaft member 58 is disposed in the center through hole 57*h* and integrally fixed through bonding, for example.

The shaft member 58 is formed to have a smaller diameter than the width of the guide groove 25 and includes a flange 58*f* at a predetermined position which is an intermediate portion. The stopper arrangement member 55 is cylindrical and fixed into, for example, an arrangement hole formed in the integral fixing section 52. Reference numeral 55*h* denotes a center through hole which communicates the interior of the concave portion with the outside. One end side of the shaft member 58 also passes through the center through hole 55*h*.

The spring 56 is disposed between a concave portion bottom surface 55*b* of the stopper arrangement member 55 and the flange 58*f* of the shaft member 58. The other end portion of the shaft member 58 is configured to be disposed in the locking hole 26 by an urging force of the spring 56. By moving the holding member 57 in an arrow Y5 direction against the urging force of the spring 56, a predetermined gap is formed between the other end face of the shaft member 58 and the bottom surface of the guide groove 25.

That is, as shown in FIG. 5, by moving the holding member 57 in the arrow Y5 direction, it is possible to attach/detach the integral fixing section 52 to/from the mounting section 19.

A state in which the other end portion of the shaft member 58 is disposed in the locking hole 26 by the urging force of the spring 56 is a state in which the integral fixing section 52 is integrally fixed to the mounting section 19 and the endoscope 10 is integrally mounted on the endoscope guide tube 50.

A configuration and operation of a detection section in the state in which the endoscope guide tube 50 is integrally mounted on the endoscope insertion portion 11 will be described with reference to FIG. 6.

The endoscope system 1 of the present embodiment is provided with detection sections 60, 70 and 80 that detect that a breakage, a so-called perforation occurs in the second heat shrinkable tube 51*h*2 making up the outermost layer of the tube insertion portion 51 of the endoscope guide tube 50, and the metal wire 51R of the braid 51*b* is exposed.

The first detection section 60 is a short circuit detection section that detects whether the odd-numbered metal wires 51R1, 51R3, 51R5, 51R7 and the even-numbered metal wires 51R2, 51R4, 51R6, 51R8 of the metal wires 51R1, . . . , 51R8 making up the braid 51b which is exposed due to a perforation are short-circuited.

The first contact 35 and the second contact 36 are connected to the first detection section 60 provided in the integral fixing section 52 via the mounting section first electric contact 21a and the mounting section second electric contact 21b.

After a supply voltage Vcc supplied from a power source section of the apparatus body 40 is converted to an AC power source, power is supplied to the first detection section 60 via the transmission coil 59 and the reception coil 28 making up a non-contact power supply section 61.

A smoothing circuit made up of a diode 62D and a capacitor 63C is connected to the reception coil 28 of the non-contact power supply section 61. A smoothed supply voltage appears at the capacitor 63C.

The first contact 35 is connected to one end of the capacitor 63C and the second contact 36 is connected to the other end (reference potential end) of the capacitor 63C via a first resistor 64R.

When neighboring metal wires 51R of the braid 51b are short-circuited, a current flows from one end of the capacitor 63C to the other end of the capacitor 63C via the first contact 35, for example, one metal wire 51R3 in contact with a live part, the live part (not shown), the other metal wire 51R4, the second contact 36, and the first resistor 64R.

A first current detection amplifier 65 is connected to both ends of the first resistor 64R. The first current detection amplifier 65 detects the current flowing through the first resistor 64R and outputs an output corresponding to the current value to one input end of a comparator 66.

Resistors 67R1 and 67R2 are connected to both ends of the capacitor 63C. A connection point of the resistors 67R1 and 67R2 is connected to the other input end of the comparator 66. Through resistance voltage division of the resistors 67R1 and 67R2, a preset constant voltage is applied to the other input end of the comparator 66.

The comparator 66 outputs high level H or low level L according to the level of the one input end and the other input end.

For example, if no current is flowing through the first resistor 64R, the output of the first current detection amplifier 65 is lower than the constant voltage applied to the other input end of the comparator 66 and the output of the comparator 66 is at low level L. On the other hand, when a current flows through the first resistor 64R, the output of the first current detection amplifier 65 is higher than the constant voltage applied to the other input end of the comparator 66. Therefore, the output of the comparator 66 is at high level H in this case.

The output end of the comparator 66 is connected to a reference potential end of the capacitor 63C via a light emitting section 68a and a fourth resistor 69 of a photocoupler 68.

The light emitting section 68a of the photocoupler 68 is caused to emit light when the output of the comparator 66 becomes high level H and sends a detection signal to a light-receiving section 68b.

Note that when the output of the comparator 66 is at low level L, the light-receiving section 68b of the photocoupler 68 is in an off state.

The output end of the light-receiving section 68b of the photocoupler 68 is connected to a first logic circuit 91 configured on the operation portion 12 side.

The first logic circuit 91 is a signal output section and configured so that the output end thereof is a logical value "0" when the light-receiving section 68b of the photocoupler 68 is in an off state and a logical value "1" when a detection signal is transmitted to the light-receiving section 68b.

The output of the first logic circuit 91 is then added to an OR circuit 94 which is a signal output section.

A second detection section 70 is a first contact side conduction detection section that detects whether or not a live part is in contact with any one of the metal wires 51R1, 51R3, 51R5 and 51R7 arrayed in odd numbers of the braid 51b which is exposed due to a perforation.

The first contact 35 is connected to the second detection section 70 configured in the operation portion 12 via a contact and wiring which are not shown.

To be more specific, when the live part comes into contact with any one of the metal wires 51R1, 51R3, 51R5 and 51R7 and a voltage is applied to the first contact 35, the first contact 35 is connected to a reference potential point via a second detection section neon lamp 71 and a second detection section resistor 72R, which perform current detection.

When a predetermined voltage is applied, the second detection section neon lamp 71 is brought into conduction and a current flows through the second detection section resistor 72R. In this case, the second detection section neon lamp 71 emits light.

A second current detection amplifier 73 is connected to both ends of the second detection section resistor 72R. The second current detection amplifier 73 detects the current flowing through the second detection section resistor 72R and outputs an output corresponding to the current value thereof to the one input end of a second detection section comparator 92.

The output of the second current detection amplifier 73 is supplied to the second detection section comparator 92 and the output of the second detection section comparator 92 is added to the OR circuit 94.

A third detection section 80 is a second contact side conduction detection section that detects whether or not a live part is in contact with any one of the metal wires 51R2, 51R4, 51R6 and 51R8 arrayed in even numbers of the braid 51b which is exposed due to a perforation.

The second contact 36 is connected to the third detection section 80 configured in the operation portion 12 via a contact and wiring which are not shown.

To be more specific, when the live part comes into contact with any one of the metal wires 51R2, 51R4, 51R6 and 51R8 and a voltage is applied to the second contact 36, the second contact 36 is connected to a reference potential point via a third detection section neon lamp 81 and a third detection section resistor 82R, which perform current detection.

When a predetermined voltage is applied, the third detection section neon lamp 81 is brought into conduction and a current flows through the third detection section resistor 82R. In this case, the third detection section neon lamp 81 emits light.

A third current detection amplifier 83 is connected to both ends of the third detection section resistor 82R. The third current detection amplifier 83 detects the current flowing through the third detection section resistor 83R and outputs an output corresponding to the current value thereof to the one input end of a third detection section comparator 93.

The output of the third current detection amplifier 83 is supplied to the third detection section comparator 93. The output of the third detection section comparator 93 is added to the OR circuit 94.

A predetermined constant voltage obtained by resistively dividing the supply voltage Vcc supplied from the power source section of the apparatus body 40 is applied to the second and third detection section comparators 92 and 93. The second and third detection section comparators 92 and 93 are signal output sections which compare this predetermined voltage with the outputs of the second and third current detection amplifiers 73 and 83 respectively and output logical values of the comparison results.

For example, the second detection section comparator 92 outputs a logical value "0" according to the output of low level L from the second current detection amplifier 73 and outputs a logical value "1" according to the output of high level H.

Similarly, the third detection section comparator 93 outputs a logical value "0" according to the output of low level L from the third current detection amplifier 83 and outputs a logical value "1" according to the output of high level H.

The OR circuit 94 to which the output from the first logic circuit 91, and the outputs from the second and third detection section comparators 92 and 93 are added, outputs high level H when any one of the output from the first logic circuit 91, and the outputs from the second and third detection section comparators 92 and 93 is "1" or outputs low level L when all the inputs are "0."

The output from the OR circuit 94 is connected to a reference potential point via a resistor 95R and an LED 96. When the output of the OR circuit 94 is at high level H, the LED 96 which is a notification section turns on.

Thus, the braid 51b making up the tube insertion portion 51 of the endoscope guide tube 50 is configured by braiding, into a tubular form, metal wires 51R in the number of a plurality of carriers wound in one direction and insulating wires 51L in the number of a plurality of carriers wound in the other direction. In addition, the plurality of metal wires 51R arrayed in parallel and wound are divided into, for example, a plurality of odd-numbered metal wires 51R and a plurality of even-numbered metal wires 51R, the plurality of odd-numbered metal wires are connected to the first contact 35 and the plurality of even-numbered metal wires are connected to the second contact 36.

The first detection section 60 is configured for the endoscope guide tube 50, which detects whether or not the neighboring metal wires 51R making up the braid 51b which is exposed due to a perforation in the second heat shrinkable tube 51h2 are short-circuited.

On the other hand, the second detection section 70 that detects whether the live part is in contact with one of the odd-numbered metal wires 51R of the braid 51b which is exposed due to a perforation, the third detection section 80 that detects whether the live part is in contact with one of the even-numbered metal wires 51R of the exposed braid 51b, and the notification lamp 22 that notifies that the second heat shrinkable tube 51h2 is broken and the metal wire 51R of the braid 51b is exposed, are provided on the operation portion 12 side.

When performing an endoscope observation on a device including a live part, the endoscope guide tube 50 is attached to the endoscope 10 in a predetermined state.

As a result, the endoscope insertion portion 11 is protected by the endoscope guide tube 50 preventing a breakage in the bending tube 15c and the heat shrinkable tube 16h that makes up the outer layer of the endoscope insertion portion 11.

Furthermore, when the notification lamp 22 turns on, the user can determine that a breakage occurs in the second heat shrinkable tube 51h2 making up the outer layer of the tube insertion portion 51 of the endoscope guide tube 50. In addition, when the notification lamp 22 is on and the second detection section neon lamp 71 of the second detection section 70 confirms the light emission, it is thereby possible to determine that the live part is in contact with a metal wire 51R arrayed in an odd number making up the braid 51b, and when the notification lamp 22 is on and light emission of the neon lamp 81 of the third detection section 80 is confirmed, it is thereby possible to determine that the live part is in contact with a metal wire 51R arrayed in an even number making up the braid 51b, and when none of the neon lamps 71 and 81 is not emitting light and only the notification lamp 22 is on, it is possible to determine that the metal wires 51R making up the braid 51b are short-circuited.

When the user who has confirmed turning on of the notification lamp 22 immediately stops operation, it is possible to prevent any accident. Moreover, by replacing the endoscope guide tube 50 by a new one, it is possible to continue to perform the inspection.

Note that in the aforementioned embodiment, the metal wires 51R arrayed so as to be able to detect a short-circuit between neighboring metal wires are alternately connected to the first connection section 31 and the second connection section 32. However, the metal wires 51R connected to the first connection section 31 and the second connection section 32 are not limited to the alternate connections, but may be connected to the first connection section 31 and the second connection section 32 in sets of two metal wires each.

As a result, it is possible to reduce the number of the connection sections 31 and 32 and connect the two metal wires 51R to the connection section and improve operability. When the number of carriers is large, three or more metal wires 51R may be connected to one connection section.

In the aforementioned embodiment, although a notification lamp is used as the notification section, the notification section is not limited to a lamp but notification may be performed using an alarm sound, speech, vibration, or the like.

In the aforementioned embodiment, the first detection section 60, the second detection section 70 and the third detection section 80 are provided in the endoscope system 1. However, when the endoscope system 1 is specialized to use in a device such as an electric car having a live part which does not use a reference potential point as ground, only the first detection section 70 may be configured without configuring the second detection section 70 and the third detection section 80.

Figure 7:
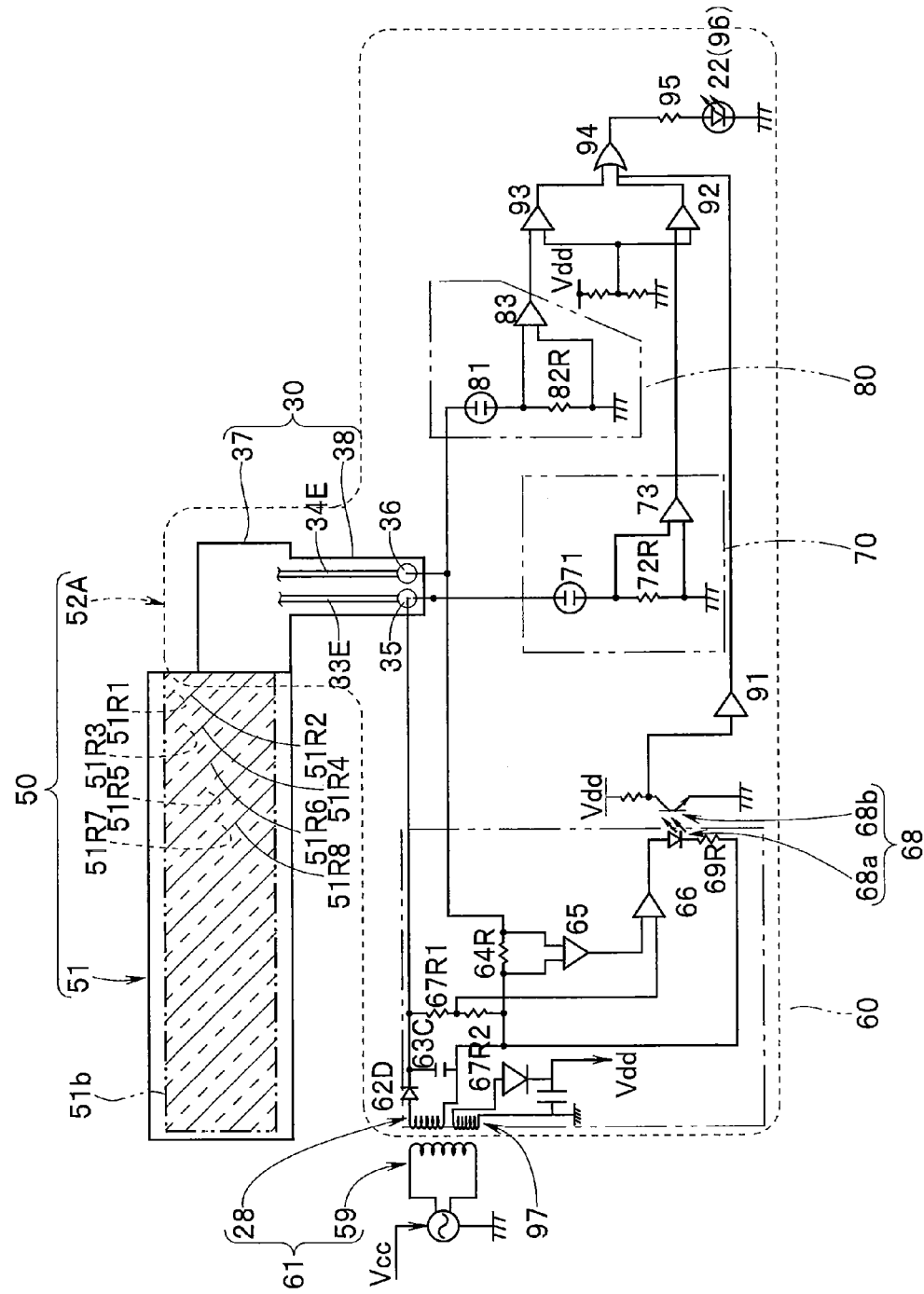
FIG. 7 is a diagram describing a configuration example of the endoscope guide tube provided with three detection sections and notification lamps.

Furthermore, in the aforementioned embodiment, the first detection section 60 is configured in the endoscope guide tube 50, the second detection section 70 and the third detection section 80 are configured on the operation portion 12 side and the notification lamp 22 is provided. However, as shown in FIG. 7, the first detection section 60, the second detection section 70, and the third detection section 80 may be configured in the integral fixing section 52A of the endoscope guide tube 50 and the notification lamp 22 may be provided.

In this configuration, after the supply voltage Vcc supplied from the power source section of the apparatus body 40 is converted to an AC power source as described above, power is supplied to the first detection section 60 via the transmission coil 59 and the reception coil 28 making up the non-contact power supply section 61. On the other hand, after the supply voltage Vcc is converted to an AC power source, a predetermined constant voltage obtained by resistively dividing the supply voltage Vdd supplied via the transmission coil 59 and the second reception coil 97 making up the non-contact power supply section 61 is applied to the detection section comparators 92 and 93.

Figure 6:
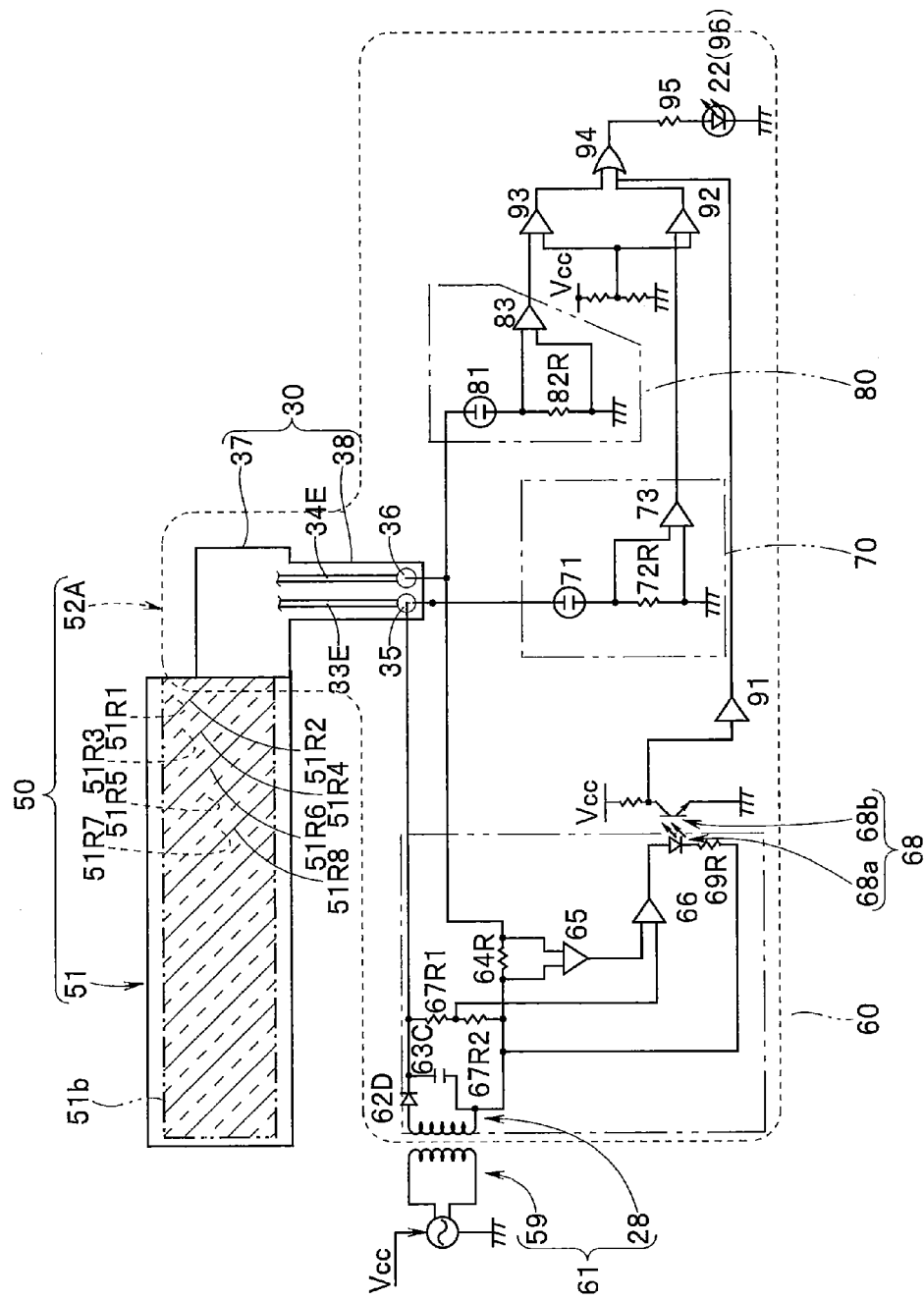
FIG. 6 is a diagram describing a detection section provided on the endoscope guide tube and the endoscope.

The rest of the configuration is similar to that in FIG. 6 and the same members are assigned the same reference numerals and description thereof will be omitted.

According to this configuration, since the operation portion 12 is configured by providing the mounting section first electric contact 21a and the mounting section second electric contact 21b in the operation portion 12 and providing the transmission coil 59 for the non-contact power supply section 61 in the operation portion 12, it is possible to drastically simplify the configuration of the operation portion 12.

Other operations and effects are similar to those of the aforementioned embodiment.

Figure 8:
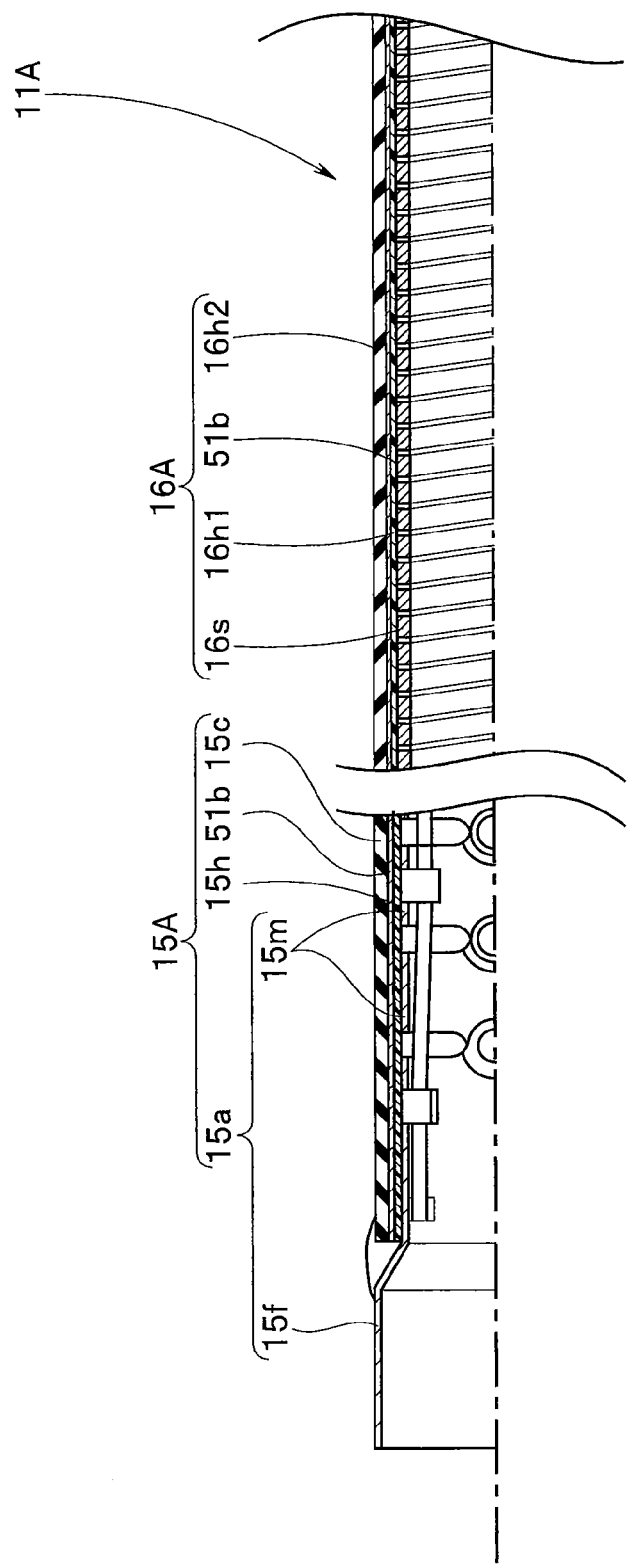
FIG. 8 is a diagram describing an endoscope insertion portion covered with a braid formed by braiding metal wires and insulating wires in the bending portion and the flexible tube portion.

Furthermore, the endoscope insertion portion 11 making up the endoscope 10 may be configured as an endoscope insertion portion 11A in a configuration substantially similar to the tube insertion portion 51 as shown in FIG. 8.

To be more specific, a bending portion 15A of the endoscope insertion portion 11A is constructed by laminating the bending piece set 15a which is constructed by rotatably connecting the distal end bending piece 15f, the plurality of intermediate bending pieces 15m and the proximal end bending piece (not shown) so as to bend up and down, a heat shrinkable tube 15h which is an insulating member that covers the outer layer of the plurality of intermediate bending piece sets 15m, the aforementioned braid 51b which is a braided tube that covers the outer layer of the heat shrinkable tube 15h, and the bending tube 15c configured of an insulating member that covers the outer layer of the braid 51b.

The flexible tube portion 16A is configured by laminating the spiral tube 16s, a first heat shrinkable tube 16h1 that covers the outer layer of the spiral tube 16s, the braid 51b that covers the outer layer of the first heat shrinkable tube 16h1, and a second heat shrinkable tube 16h2 that covers the outer layer of the braid 51b.

That is, in the embodiment, one elongated braid 51b is provided in the lower layer of the bending tube 15c making up the bending portion 15A and in the lower layer of the second heat shrinkable tube 16h2 making up the flexible tube portion 16A.

Figure 9:
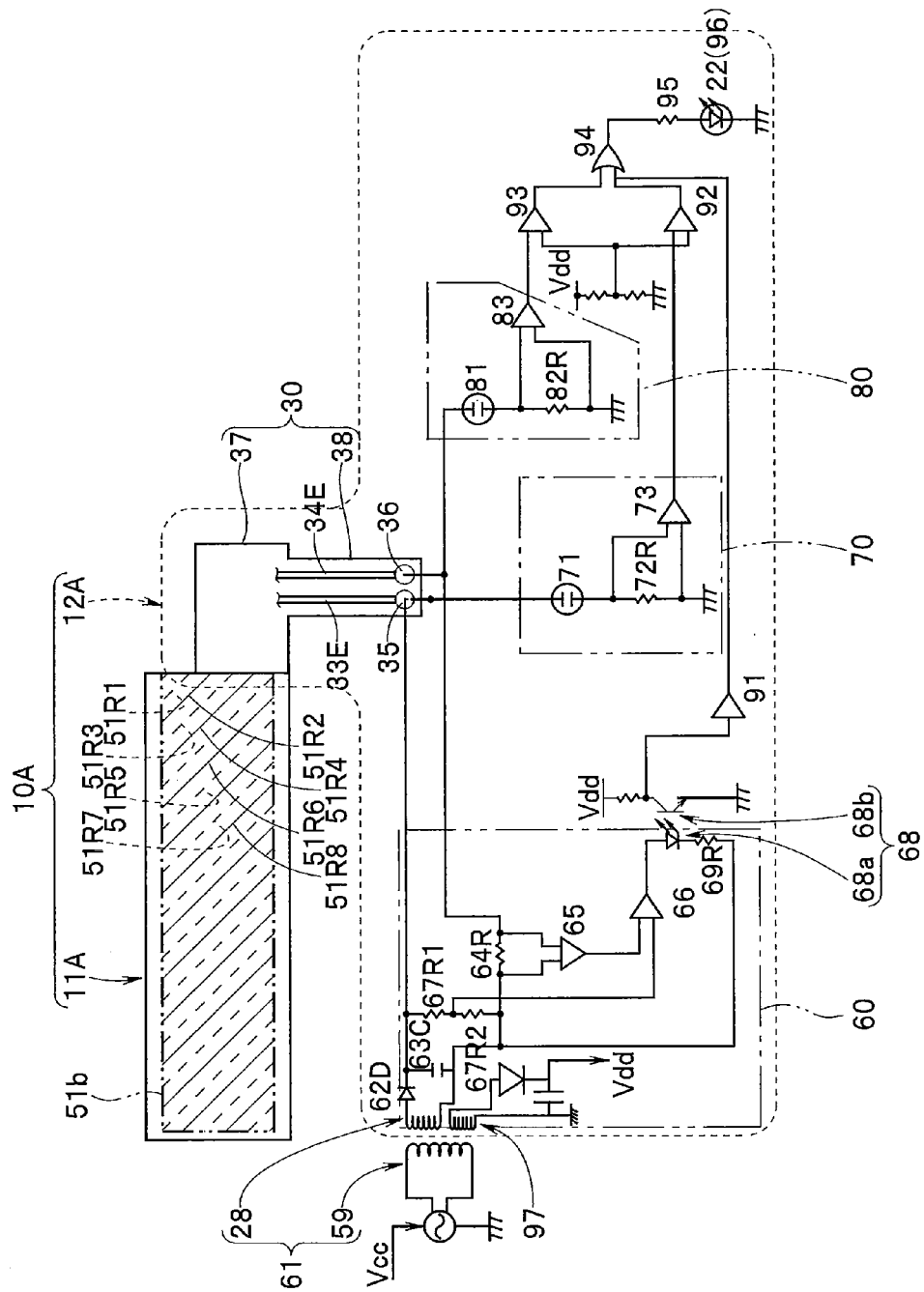
FIG. 9 is a diagram describing a configuration example in which the endoscope is provided with three detection sections and notification lamps.

As shown in FIG. 9, the aforementioned first detection section 60, second detection section 70, and third detection section 80 are configured in the operation portion 12A of the endoscope 10A provided with the endoscope insertion portion 11A and the notification lamp 22 is also provided.

Note that in the endoscope 10A of the present embodiment, the mounting section 19 provided in the operation portion 12 for disposing the integral fixing section 52 of the endoscope guide tube 50, the positioning mounting groove 20, the mounting section first electric contact 21a, and the mounting section second electric contact 21b are removed because they are unnecessary.

The rest of the configuration is similar to that of the aforementioned embodiment and the same members are assigned the same reference numerals and description thereof will be omitted.

According to this configuration, when the bending tube 15c or the second heat shrinkable tube 16h2 making up the outer layer of the endoscope insertion portion 11 is broken, the notification lamp 22 turns on, and so the endoscope 10A can determine the occurrence of the breakage.

Note that the present invention is not limited to only the above-described embodiment, but may be modified and carried out in various ways without departing from the spirit and scope of the invention.

What is claimed is:

1. A tube for use in an endoscopic instrument, the tube comprising:
   a tube member to be inserted into a device including a part through which electricity is conducted, the tube member comprising:
      a tube body made of an insulating member that makes up an outer layer; and
      a braid that makes up an inner layer of the tube body, the inner layer braids, into a tubular form:
         a plurality of metal members wound in a first direction; and
         a plurality of insulating members wound in a second direction opposite to the first direction of the plurality of metal members;
   a connection member provided with a first contact electrically connecting in a bundled manner ends of a first group of the plurality of metal members and a second contact electrically connecting in a bundled manner ends of a second group of the plurality of metal members; and
   at least one of a first contact side conduction detection circuit configured to detect that the part contacts any of the first group of the plurality of metal members connected to the first contact and a second contact side conduction detection circuit configured to detect that the part contacts any of the second group of the plurality of metal members connected to the second contact.

2. The tube according to claim 1, further comprising a short circuit detection circuit configured to detect a short circuit state in which the part is in contact with any of the first group of the plurality of metal members connected to the first contact and any of the second group of the plurality of metal members connected to the second contact.

3. The tube according to claim 1, wherein the connection member comprising the first contact and the second contact is a flexible substrate disposed on a proximal end side of the tube member, the flexible substrate comprises:
   a plurality of first connection sections to which the ends of the first group of the plurality of metal members are connected, respectively;
   a plurality of second connection sections to which the ends of the second group of the plurality of metal members are connected, respectively;
   a first wiring that electrically connects the plurality of first connection sections and the first contact; and
   a second wiring that electrically connects the plurality of second connection sections and the second contact.

4. The tube according to claim 1, wherein a number of the ends of the plurality of metal members and a number of ends of the plurality of insulating members are adjusted to adjust a balance between the plurality of metal members wound in the first direction and the plurality of insulating members wound in the first direction making up the braid.

5. The tube according to claim 1, wherein wire diameters of the plurality of metal members and wire diameters of the plurality of insulating members are adjusted to adjust a balance between the plurality of metal members wound in the first direction and the plurality of insulating members wound in the first direction up the braid.

6. The tube according to claim 1, further comprising a notification circuit that performs notification when one or more of the first contact side conduction detection circuit detects that any of the first group of the plurality of metal members are in contact with the part and the second conduction detection circuit detects that any of the second group of the plurality of metal members are in contact with the part.

7. An endoscope guide tube comprising:
a fixing section; and
a tube insertion portion fixed to a distal end of the fixing section, the tube insertion portion having an interior lumen for passage of an endoscope;
wherein the tube insertion portion comprises the tube of claim 1.

8. An endoscope comprising:
an operation portion; and
an insertion portion fixed to a distal end of the operating portion;
wherein the insertion portion comprises the tube of claim 1.

9. A tube for use in an endoscopic instrument, the tube comprising:
a tube member to be inserted into a device including a part through which electricity is conducted, the tube member comprising:
tube body made of an insulating member that makes up an outer layer; and
a braid that makes up an inner layer of the tube body, the inner layer braids, into a tubular form:
a plurality of metal members wound in a first direction; and
a plurality of insulating members wound in a second direction opposite to the first direction of the plurality of metal members;
a connection member provided with a first contact electrically connecting in a bundled manner ends of a first group of the plurality of metal members and a second contact electrically connecting in a bundled manner ends of a second group of the plurality of metal members; and
a short circuit detection circuit configured to detect a short circuit state in which the part is in contact with any of the first group of the plurality of metal members connected to the first contact and any of the second group of the plurality of metal members connected to the second contact.

10. The tube according to claim 9, wherein the plurality of metal members are arranged in an array with individual metal members of the first group of the plurality of metal members being positioned between individual metal members of the second group of the plurality of metal members.

11. The tube according to claim 9, further comprising a notification circuit that performs notification when the short circuit detection circuit detects that any of the first group of the plurality of metal members connected to the first contact and the any of the second group of the plurality of metal members connected to the second contact are short-circuited.

12. The tube according to claim 9, wherein the connection member comprising the first contact and the second contact is a flexible substrate disposed on a proximal end side of the tube member, the flexible substrate comprises:
a plurality of first connection sections to which the ends of the first group of the plurality of metal members are connected, respectively;
a plurality of second connection sections to which the ends of the second group of the plurality of metal members are connected, respectively;
a first wiring that electrically connects the plurality of first connection sections and the first contact; and
a second wiring that electrically connects the plurality of second connection sections and the second contact.

13. The tube according to claim 9, wherein a number of the ends of the plurality of metal members and a number of ends of the plurality of insulating members are adjusted to adjust a balance between the plurality of metal members wound in the first direction and the plurality of insulating members wound in the first direction making up the braid.

14. The tube according to claim 9, wherein wire diameters of the plurality of metal members and wire diameters of the plurality of insulating members are adjusted to adjust a balance between the plurality of metal members wound in the first direction and the plurality of insulating members wound in the first direction making up the braid.

15. An endoscope guide tube comprising:
a fixing section; and
a tube insertion portion fixed to a distal end of the fixing section, the tube insertion portion having an interior lumen for passage of an endoscope;
wherein the tube insertion portion comprises the tube of claim 9.

16. An endoscope comprising:
an operation portion; and
an insertion portion fixed to a distal end of the operating portion;
wherein the insertion portion comprises the tube of claim 9.

* * * * *